US011806122B2

(12) United States Patent
Maitre et al.

(10) Patent No.: US 11,806,122 B2
(45) Date of Patent: Nov. 7, 2023

(54) UTILIZATION OF INFANT ACTIVATED AUDIO PLAYER

(71) Applicant: THE RESEARCH INSTITUTE AT NATIONWIDE CHILDREN'S HOSPITAL, Columbus, OH (US)

(72) Inventors: Nathalie Linda Maitre, Columbus, OH (US); Olena D. Chorna, Tallahassee, FL (US)

(73) Assignee: The Research Institute at Nationwide Children's Hospital, Columbus, OH (US)

(*) Notice: Subject to any disclaimer, the term of this patent is extended or adjusted under 35 U.S.C. 154(b) by 885 days.

(21) Appl. No.: 16/753,999

(22) PCT Filed: Oct. 9, 2018

(86) PCT No.: PCT/US2018/055017
§ 371 (c)(1),
(2) Date: Apr. 6, 2020

(87) PCT Pub. No.: WO2019/071271
PCT Pub. Date: Apr. 11, 2019

(65) Prior Publication Data
US 2020/0390659 A1 Dec. 17, 2020

Related U.S. Application Data

(60) Provisional application No. 62/569,088, filed on Oct. 6, 2017.

(51) Int. Cl.
A61B 5/03 (2006.01)
A61J 17/00 (2006.01)
(Continued)

(52) U.S. Cl.
CPC ............ *A61B 5/038* (2013.01); *A61J 17/001* (2015.05); *A61J 17/1011* (2020.05);
(Continued)

(58) Field of Classification Search
CPC .. A61J 17/001; A61J 17/1011; A61J 2200/70; A61B 5/038; A63F 3/0402; G06F 3/165; G06F 3/167; H04R 1/028
See application file for complete search history.

(56) References Cited

U.S. PATENT DOCUMENTS 4,221,927 A    9/1980  Dankman et al.
4,554,919 A *  11/1985 Hubert ................. A61J 17/1011
                                              606/234
(Continued)

FOREIGN PATENT DOCUMENTS

BR  11 2020 004714-7  10/2018
DE        20207457    9/2002
GB         2472439 A  2/2011

OTHER PUBLICATIONS

Technical Examination Report, Written Opinion in Brazilian Patent Application No. BR 11 2020 004714-7, dated Nov. 25, 2022, by means of the petition No. 870220109752, in response to the written opinion Issued under Ordinance No. 34/2022. (5 pages).
(Continued)

*Primary Examiner* — Jason R Kurr
(74) *Attorney, Agent, or Firm* — Watts Law LLC; John A. Yirga, Esq.

(57) ABSTRACT

One aspect of the present disclosure include a method of utilizing an oro-motor device to activate an audio device, the method includes providing an oro-motor device having a sensor and a nipple; producing a signal when the nipple portion present in an infants mouth when the nipple portion yields a first measured pressure over an age appropriate predetermined threshold applied to the nipple portion by the
(Continued)

infant; responsive to the signal, playing an age appropriate audio recording for a predetermined duration on an audio device; and raising the age appropriate predetermined threshold to a raised threshold proportionally to a difference between the first measured pressure application to the nipple portion and the age appropriate predetermined threshold.

20 Claims, 7 Drawing Sheets

(51) Int. Cl.
   *G06F 3/16* (2006.01)
   *A63F 3/04* (2006.01)
(52) U.S. Cl.
   CPC .............. *G06F 3/165* (2013.01); *G06F 3/167* (2013.01); *A61J 2200/70* (2013.01); *A63F 3/0402* (2013.01)

(56) References Cited

U.S. PATENT DOCUMENTS

| | | | |
|---|---|---|---|
| 4,819,616 A | 4/1989 | Samson | |
| 5,292,335 A * | 3/1994 | Shin | A61J 17/1011 606/234 |
| 5,782,867 A * | 7/1998 | Shrock | A61J 17/1011 606/234 |
| 5,830,235 A | 11/1998 | Standley | |
| 7,211,102 B2 | 5/2007 | DeSousa et al. | |
| 10,772,533 B2 * | 9/2020 | Werzowa | B60W 40/08 |
| 2005/0225951 A1 | 10/2005 | Kurakami | |
| 2006/0079814 A1 | 4/2006 | Barlow et al. | |
| 2006/0194506 A1 | 8/2006 | Sacchetti | |
| 2008/0077183 A1 | 3/2008 | Cohen | |
| 2012/0244969 A1 | 9/2012 | Binder | |
| 2013/0059284 A1 | 3/2013 | Giedgowd, Jr. et al. | |
| 2014/0309063 A1 | 10/2014 | Molina | |
| 2015/0248828 A1 | 9/2015 | Cloutier et al. | |
| 2015/0250978 A1 | 9/2015 | Pelsue et al. | |
| 2017/0020788 A1 * | 1/2017 | Malone | A61J 17/1011 |

OTHER PUBLICATIONS

Saint-Georges, C., Chetouani, M., Cassel, R., Apicella, F., Mahdhaoui, A. (2013) Motherese in Interaction: At the Cross-Road of Emotion and Cognition? (A Systemic Review). PLOS One 8(10): e78103. https://doi.org/10.1371journal.pone.0078103. Published Oct. 2013.
Kovacs, A.M., and Mekler, J. "Cognitive Gains in 7-Month-Old Bilingual Infants." Proc. Natl. Acad. Sci. U.S.A. (Apr. 21, 2009) 106(16): pp. 6556-6560. doi:10.1073/pnas.0811323106. Published online Apr. 13, 2009.
Kalashnikova, Marina et al. "Infant-Directed Speech Facilitates Seven-Month-Old Infants' Cortical Tracking of Speech." Scientific Reports, vol. 8, No. 1, 2018, doi:10.1038/s41598-018-32150-6. Published May 2012.
International Search Report and Written Opinion of the International Searching Authority dated Jan. 16, 2019 for PCT International Application No. PCT/US2018/55017, filed Oct. 9, 2018. (9 pages).
European Office Action for EP Application No. 18864381.1 dated May 20, 2021 (11 pages).

* cited by examiner

UTILIZATION OF INFANT ACTIVATED AUDIO PLAYER

CROSS REFERENCE TO RELATED APPLICATIONS

The following application claims priority under 35 U.S.C. § 371 to international PCT application serial number PCT/US18/55017 filed Oct. 9, 2018 entitled UTILIZATION OF INFANT ACTIVATED AUDIO PLAYER that was published on Apr. 11, 2019 under international publication number WO/2019/071271, which claims priority under 35 U.S.C. § 119 (e) to U.S. Provisional Patent Application Ser. No. 62/569,088 filed Oct. 6, 2017 entitled UTILIZATION OF INFANT ACTIVATED AUDIO PLAYER. Priority is claimed for all the above-identified applications and publication, all of which are incorporated herein by reference in their entireties for all purposes.

TECHNICAL FIELD

The present disclosure generally relates to an audio device and sensor combination, and more particularly to an audio device and sensor combination for use in neonatal care with and without a system used to stimulate and improve speech sound differentiation in infants, preterm infants, and/or premature infants using oro-motor responses.

BACKGROUND

Research has shown that preterm and premature infants and/or infants born with neurological insult have delay and/or impairment resulting from hospitalization (e.g., hospitalization necessary for survival). The lack of audio interaction, particularly parental audio interaction, is a major contributor to developmental delay and/or impairment. Infants lacking such audio interaction tend to have inferior speech sound differentiation. There is a temporal window at which speech sound differentiation occurs in both infants and preterm infants. During that temporal window, sound differentiation is attenuated in preterm infants compared to term infants. The attenuated sound differentiation in preterm infants predicts inferior language outcomes at two years of age.

Generally, preterm and premature infants are housed in small isolettes or cribs. The preterm and premature infants are held skin-to-skin two to three times per day for about forty-five (45) minutes. These preterm and premature infants often lack parental interaction, and thus, normal parental stimuli and the resulting benefits of such interaction.

SUMMARY

One aspect of the present disclosure comprises a method of utilizing an oro-motor device to activate an audio device, the method includes providing an oro-motor device, comprising a sensor and a depressible portion, producing an output signal when the depressible portion is compressed yielding a first measured pressure over an age appropriate predetermined threshold applied to the depressible portion, responsive to the output signal, playing an age appropriate audio recording for a predetermined duration on an audio device and increasing the age appropriate predetermined threshold to a raised threshold proportionally to a difference between the first measured pressure to the depressible portion and the age appropriate predetermined threshold.

Another aspect of the present disclosure comprises a non-transitory computer readable medium storing machine executable instructions for utilizing an oro-motor device to activate an audio device, The non-transitory computer readable medium storing machine executable instructions comprising a language system in electronic communication with an audio device, a sensing device comprising a sensor, and an interface, the interface configured to receive user data and the sensing device configured to send signals to the language system, the language system providing at least one of a first recommendation or a second recommendation for sensing device sensor usage, a sensor threshold and sensor readings of the sensing device, a duration of audio output, and identifies specific parameters for audio output. The language system based upon the signal from the sensing device indicating the sensor threshold has been exceeded, sends instructions to the audio device to emit an appropriate audio recording that conforms to the specific parameters for audio output for the assigned duration of audio output.

Yet another aspect of the present disclosure comprises a language system comprising an audio device coupled an oro-motor device. The system comprising the oro-motor device comprising a nipple housing a sensor, wherein the sensor produces an output signal when said nipple portion is compressed to a pressure over a first measured pressure over an age appropriate predetermined threshold. The audio device comprising a microcomputer in electrical communication with the oro-motor device, a microphone, a speaker, and an interface, the microcomputer comprising a language algorithm, the language system responsive to a user input received via the interface, assigns a sensor threshold and sensor readings of the oro-motor device, assigns a duration of audio output, and identifies specific parameters for audio output, the language system based upon the output signal from the oro-motor device indicating the age appropriate predetermined threshold has been exceeded, sends instructions to the audio device to emit an appropriate audio recording that conforms to the specific parameters for audio output for the assigned duration of audio output.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

Figure 1:
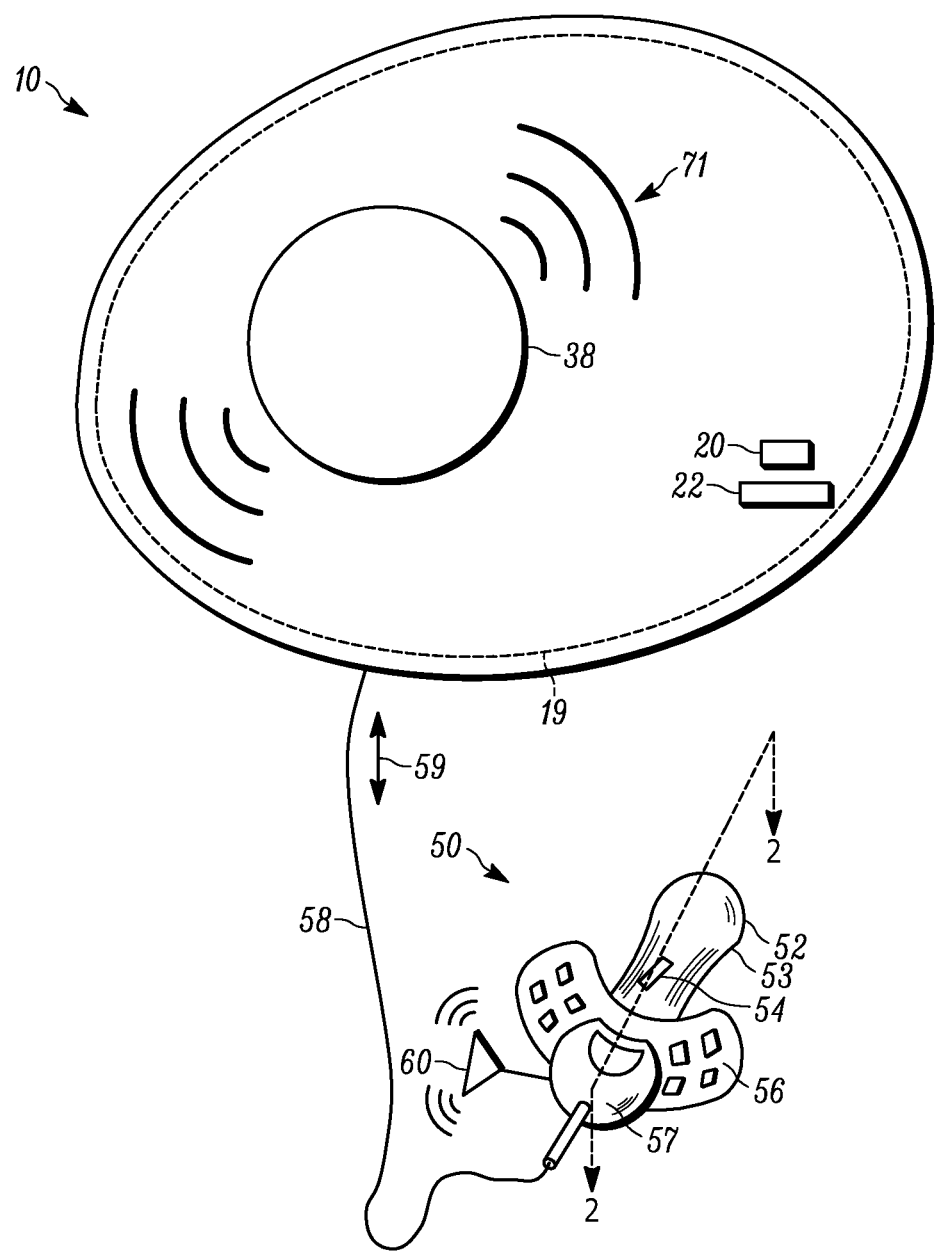
FIG. 1 illustrates a perspective view of an oro-motor device and an audio device in accordance with one example embodiment of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements throughout unless otherwise noted. The present disclosure generally relates to an audio device and sensor combination, and more particularly to an audio device and sensor combination for use in neonatal care with and without a system used to stimulate and improve speech sound differentiation in infants, preterm infants, and/or premature infants using oro-motor responses.

In FIG. 1, an infant, child, or adult activated audio player or audio device 10 comprising a rectangular shape, and housing electronic components 19, including a speaker 38, is connected to an oro-motor device or pacifier 50. The oro-motor device 50 and the audio device 10 are for promoting active learning in preterm infants by using audio output (e.g., parental speech, mother's voice, a women's voice, etc.) from the audio device to teach the preterm infant how to interact with the oro-motor device, while using the oro-motor device to teach the infant how to recognize speech (e.g., creating a learning feedback loop). Additionally, the audio device 10 comprises a system (see FIG. 9) exposing infants, children, and adults, to non-native languages, thereby increasing speech sound differentiation in infants, children, and adults in the non-native language to which they are conditioned.

In one example embodiment, the audio device 10 comprises an external material of, for example, a rubber-like or pliable polymeric material, such as polypropylene and the like. Other shapes for the audio device, such as square, spherical, ellipsoid, superegg, and superellipsoid shapes are contemplated. In one example embodiment, the audio device 10 has an overall greatest diameter, height, and/or width of about ten (10") inches. The audio device 10 comprises a plurality of spaced apart apertures 20, 22 for accessing electronic components 19, as illustrated in FIG. 5.

Figure 5:
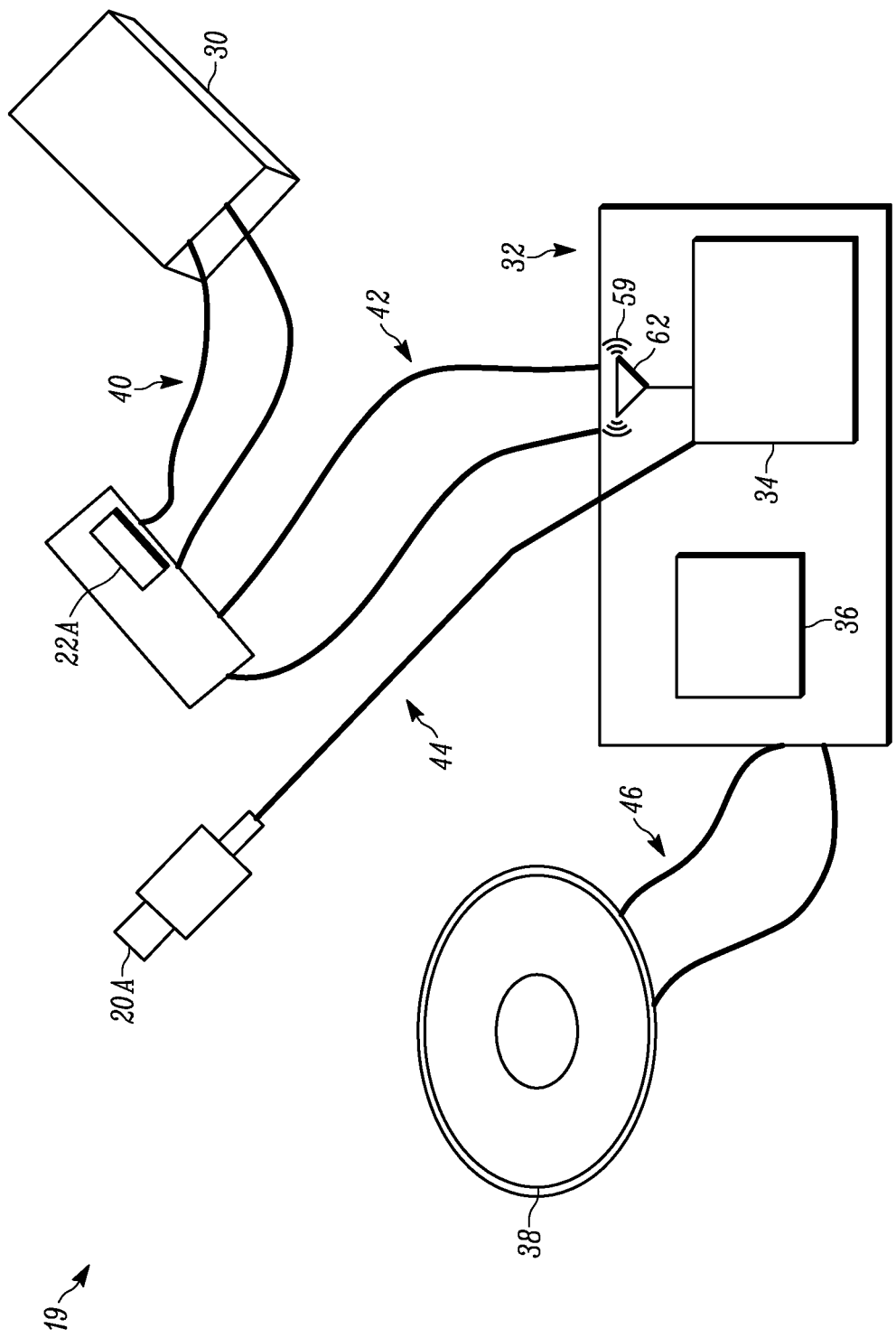
FIG. 5 illustrates an electrical schematic of electrical elements housed in an audio device in accordance with one example embodiment of the present disclosure.

In the illustrated example embodiment of FIG. 5, the first aperture 20 comprises a USB input 20A and the second aperture 22 comprises a charging input 22A for the electric components 19. In another example embodiment, the audio device 10 comprises a single aperture, and the single aperture comprises both the charging port and the USB port. In yet another example embodiment, the audio device 10 lacks an aperture. The audio device 10 comprises at least one of a short-range wireless interconnection signal transceiver 62, wherein audio input is input via the short-range wireless transceiver.

The oro-motor device 50 is in wired 58 communication with the audio device 10 and/or in wireless communication, via a transceiver 60, with the audio device. The oro-motor device 50 comprises a nipple portion 52, a sensor housing 53, a sensor 54, a guard portion 56, and a grip portion 57. In an example embodiment, such as when the oro-motor device 50 is wireless, the oro-motor device comprises a power source 64 (e.g., such as a lithium ion battery). The sensor 54 is connected to the power source 64 (see, for example, FIG. 5) and/or a power source (e.g., a battery 30, as illustrated in FIG. 5) within the audio device 10. Further, the sensor 54 is in communication and/or powered with the audio device 10 via the wire 58 or the transceiver 60. In one example embodiment, the grip portion 57 and/or the guard portion 56 comprise the transceiver 60. In another example embodiment, the grip portion 57 and/or the guard portion 56 are connected to the wire 58.

The nipple portion 52 is deformable and hollow. The nipple portion 52 comprises one or more of latex (e.g., natural latex rubber, non-vulcanized rubber, etc.), polymers (e.g., such as synthetic polymers, for example silicone), hard plastic, or the like. The guard portion 56 comprises a rigid plastic, metal, or the like. In one example embodiment, the nipple portion 52 and the guard portion 56 comprise a same material and/or a unibody design, forming the sensor housing 53. The guard portion 56 comprises openings, such that in the event of the oro-motor device 50 being swallowed, the infant's breathing is not blocked. In one embodiment, the grip portion 57 comprises a ring (not shown).

Figure 2:
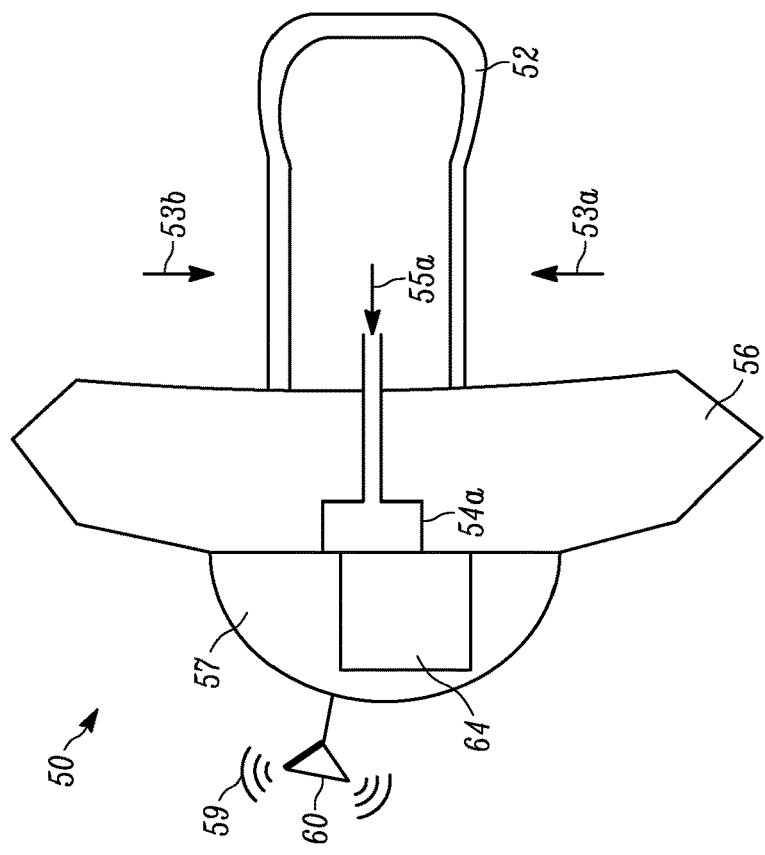
FIG. 2 illustrates the oro-motor device of FIG. 1 taken along section line 2-2 of FIG. 1 in accordance with one example embodiment of the present disclosure.

Multiple sensor 54 types are contemplated to detect when an infant or preterm infant is interacting (e.g., sucking) on the oro-motor device 50. As shown in the illustrated example embodiment of FIG. 2, an air flow sensor 54a is comprised within the oro-motor device 50. When the infant interacts by applying pressure along arrows 53a, 53b to compress the nipple portion 52, the nipple portion deforms, causing air evacuation from an internal space within the nipple portion. The air flow sensor 54a measures an amount of air and/or a rate of the air being expelled from the nipple portion 52. The air flow sensor 54a converts the amount of air and/or the speed of the air into an output signal 59 that is indicative of the pressure 53a, 53b that the infant is applying to the nipple portion 52. The output signal 59 is communicated to the audio device 10 (e.g., via wireless or wired 58 signal). In one embodiment, the transceiver 60 of the oro-motor device 50 transmits the output signal 59 to a transceiver 62 of the audio device 10 (see FIG. 5).

Figure 3:
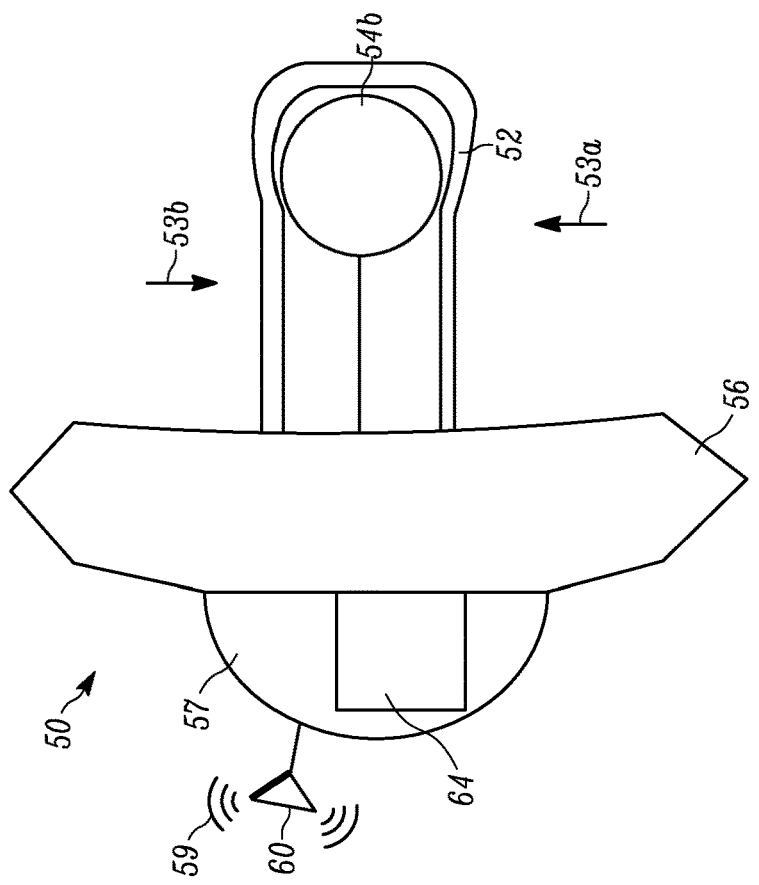
FIG. 3 illustrates the oro-motor device of FIG. 1 taken along section line 2-2 of FIG. 1 in accordance with a second example embodiment of the present disclosure.

In the illustrated example embodiment of FIG. 3, a pressure sensor 54b is within the nipple portion 52. When the infant interacts with the pressure sensor 54b, the pressure sensor measures the amount of pressure 53a, 53b that is applied to the nipple portion 52. The pressure sensor 54b converts the measured pressure into an output signal 59 that is indicative of the pressure 53a, 53b that is applied to the nipple portion 52. The output signal 59 is communicated to the audio device 10 in the same manner as described above with regard to the air flow sensor 54a.

Figure 4B:
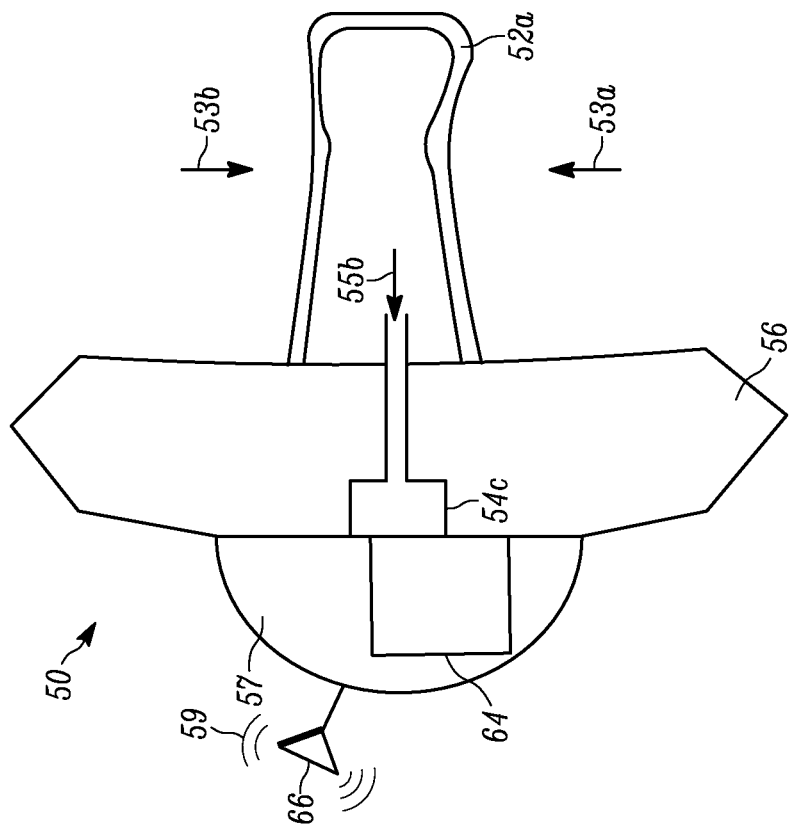
FIG. 4B illustrates the oro-motor device of FIG. 1 taken along section line 2-2 of FIG. 1 in accordance with a fourth example embodiment of the present disclosure.
Figure 4A:
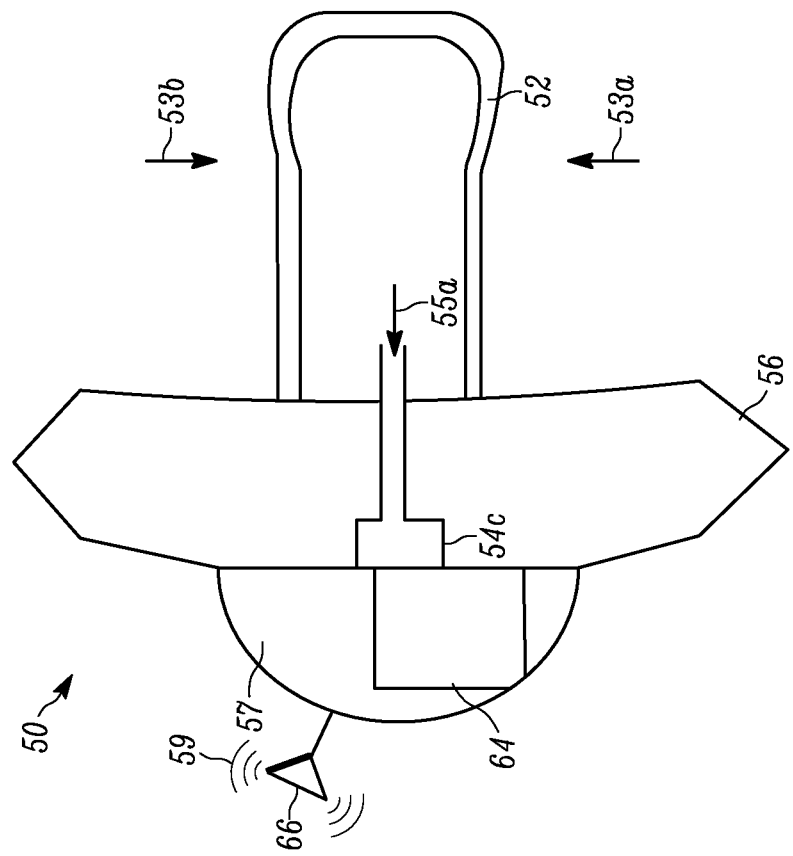
FIG. 4A illustrates the oro-motor device of FIG. 1 taken along section line 2-2 of FIG. 1 in accordance with a third example embodiment of the present disclosure.

In the illustrated example embodiment of FIGS. 4A-4B, an air evacuation sensor 54c is within the nipple portion 52. FIG. 4A illustrates the nipple portion 52 having a first internal volume prior to the infant interacting with the nipple portion. FIG. 4B illustrates the nipple portion 54*a* having a second internal volume to after the infant interacts with the nipple portion. The air evacuation sensor 54*c* monitors the amount of air evacuated, such that a total internal volume of the nipple portion 52 is known. For example, the nipple portion 54*a* having the second internal volume, will require a greater force to evacuate a first air volume than evacuating the first air volume from the nipple portion 54*a* requires.

When the infant interacts with the air evacuation sensor 54*c*, the air evacuation sensor measures the amount of pressure 53*a*, 53*b* that is applied to the nipple portion 52 by measuring the amount of air evacuated. The evacuation sensor 54*c* converts the measured pressure into an output signal 59 that is indicative of the pressure 53*a*, 53*b* that is applied to the nipple portion 52. The evacuation sensor 54*c* or a smart element of the audio device 10 and/or the pacifier 50 determines an internal volume change caused by the infant interaction, and correlates the amount of air evacuated and the current internal volume, to determine the pressure applied to the nipple portion 52 by the infant. The output signal 59 is communicated to the audio device 10 in the same manner as described above with regard to the air flow sensor 54*a*.

Turning to FIG. 5, the electrical components 19 of the audio device 10 of one example embodiment are illustrated. In the illustrated example embodiment, the electronic components 19 comprise the speaker 38 configured to emit audio, an electrical circuit 34 to convert an audio signal received through the first aperture 20 and/or a short-range wireless interconnection signal into an audio input for the speaker 38, a microcomputer 32 to receive, compare, compute, analyze, and/or interpret sensor signals from the pacifier 60 and communicate with a circuit 34, and/or a power supply, such as a battery 30 to power at least one of the electronic components. In another example embodiment, the electronic components 19 comprise a light source (not shown), such as a light emitting diode indicating that one or more features of the audio device 10 are functioning.

In one example embodiment, the speaker 38 may comprise a small box speaker, one example of a suitable small box speaker includes Dayton Audio CE38M-8 1½" Mini Speaker 8 Ohm manufactured by Dayton Audio™. The microcomputer 32 comprises a microprocessor, one such example microprocessor would be SainSmart Nano v. 3.0 manufactured by SainSmart. The electrical circuit 36 comprises a printed circuit board (PCB) consisting of an application specific integrated circuit, one such PCB would be a prototyping board having an item number: G19388. In an example embodiment, the microcomputer 32 comprises an MP3 player 36. The MP3 player 36 is in electrical communication with other elements of the electrical components 19, such as the circuit 34, the speaker 38, and/or the battery 30.

In one example embodiment, the MP3 player 36 stores and plays audio, one such MP3 player would be DiyMall Mini MP3 player manufactured by DiyMall™. In this example embodiment, the battery 30 provides power to the electrical components 19 for a duration over ten (10) hours, one such battery 30 is a lithium ion battery. It would be appreciated by one of ordinary skill in the art that many different speaker, microcomputer, circuit, and/or battery types can be utilized in this application.

In the illustrated example, the audio input for the speaker 38 comprises the USB port 20A that is accessible through the first aperture 20. The USB port 20A is in wired communication 44 with an input/output (I/O) port of the microcomputer 32. The charging input 22A for the battery 30 is in wired communication 40, 42 with the microcomputer 32 and the battery 30, respectively. The speaker 38 is in wired communication 46 with an I/O port of the microcomputer 32. In an example embodiment, the speaker 38 is in direct wired communication with the MP3 player 36.

In an example embodiment, one or more switches are in wired communication with one or more I/O ports of the microcomputer 32. Actuation of a first switch turns audio on or off, actuation of a second switch fast forwards the audio, and actuation of a third switch rewinds the audio. It would be appreciated by one of ordinary skill in the art, that the one or more switches may perform multiple functions in response to actuation, such as altering an interval setting of the audio, a volume of the audio, etc. In another example embodiment, the interval setting of the audio device 10 are programmable to control a number of times per day the audio is emitted. Additionally, the battery 30 enables the audio device 10 to be cordless, preventing dangers associated with cords, such as the infant becoming fatally tangled or constricted by a cord inside the isolette or crib.

In the illustrated example embodiment of FIG. 5, the electronic components 19 comprise an interface 37 in wired communication with an I/O port of the microcomputer 32. The interface 37 can be used to alter a duration, a decibel level, a play per day interval of the audio, and/or other assigned functions of the one or more switches. Additionally the interface 37 can be used to select one or more audio selections stored on the MP3 player and/or on a USB drive connected to the USB port 20A. In another example embodiment, the interface 37 is presented on a secondary device 39 in communication with the audio device 10 via the short-range interconnection signal.

The audio device 10 when used with infants provides a developmental brain benefit. The audio device 10 is programmed, via a language system 21 or some other program, to perform a predetermined function 67 responsive to receiving the output signal 59 from the oro-motor device 50, indicating a pressure over a pressure threshold 69 has been applied to the nipple portion 52. Wherein, the pressure threshold 69 is determined based upon an age, maturity, and/or previous pressure successfully applied by the preterm or premature infant and/or term infant, or child. Wherein, age means chronological age and/or developmental age. In one example embodiment, the predetermined function 67 is playing a pre-recorded age appropriate audio recording 71 of a caretaker's voice (e.g., a mother's voice, a relative's voice, a women's voice, etc.). The audio recording 71 is played for a predetermined amount of time (e.g., 10 seconds) and stops unless a second signal is received from the oro-motor device 50, indicating a sensed pressure over the pressure threshold 69 has again been applied to the nipple portion 52.

In another example embodiment, the microcomputer 32 of the audio device 10 is running the language system 21 that accepts parameters including, inputs, such as an infant's age, a preferred language, song duration versus reading duration, etc. The language system 21, via the microcomputer 32, is in electrical communication with an output screen, such as a screen of the secondary device 39, an attached screen, the interface 37, etc. The language system 21, via memory of the microcomputer 32, stores audio recordings in various languages, for various ages, instructions for using the language algorithm, pressure thresholds 69 associated with various ages, etc.

In one example embodiment, the secondary device 39 is a remote computer system. The computer system includes desktop, laptop, tablet hand-held personal computing device, IAN, WAN, WWW, and the like, running on any number of known operating systems and are accessible for communication with remote data storage, such as a cloud, host operating computer, via a world-wide-web or Internet. In another example embodiment, the microcomputer 32 comprises a function specific circuit board having for example, an application specific analog circuit (ASIC) that operates the language system 21.

In another example embodiment, the microcomputer 32 comprises a processor, a data storage, computer system memory that includes read-accessible-memory ("RAM"), read-only-memory ("ROM") and/or an input/output interface. The microcomputer 32 executes instructions by non-transitory computer readable medium either internal or external through the processor that communicates to the processor via input interface and/or electrical communications, such as from the secondary device 39 or the oro-motor device 50. In yet another example embodiment, the microcomputer 32 communicates with the Internet, a network such as a LAN, WAN, and/or a cloud, input/output devices such as flash drives, remote devices such as a smart phone or tablet, and displays such as the interface 37.

In one example embodiment, the language system 21, via memory of the microcomputer 32, stores audio recordings 71 in various languages, for various ages, instructions for using the language algorithm, the pressure thresholds 69 associated with various ages, etc. In another example embodiment, the language system 21 retrieves audio recordings in various languages, for various ages, instructions for using the language algorithm, the pressure thresholds 69 associated with various age that are stored remotely, such as on a cloud, or via the internet. In this example embodiment, the audio recordings 71 comprise recordings of caretakers reciting infant directed speech (e.g. "who is the hungry baby, are you the hungry baby"), wherein infant directed speech includes speech directed to infants, children, and/or adults. The audio recordings 71 comprise active reading and/or singing comprising recording sound that elicits engagement from a person who is listening.

In another example embodiment of the present disclosure, the audio recording comprises a pre-recorded age appropriate audio recording in foreign language (e.g., Spanish, French, Mandarin, Cantonese, Farsi, etc.). The foreign language audio recordings 71 comprise recordings of infant directed speech in the selected language. The foreign language audio recordings 71 comprise active reading and/or singing. Infants and/or children exposed to pre-recorded age appropriate audio recording in a given foreign language were found to have a much greater speech differentiation ability in that language after an average of twenty (20) sessions with the audio device 10 and language system 21. In one example embodiment, as session comprises exposing the infant, child, and/or adult to the pre-recorded age appropriate audio recording in foreign language. For example, an infant, child, and/or adult exposed to pre-recorded age appropriate audio recording in French showed a marked and statistically significant increase in the ability to differentiate French language than in languages that the infants were not exposed to. Further, there were no deleterious outcomes, such as the infant or child increasing sound differentiation in the foreign language at the expense of poorer outcomes in the infant or child's native language.

Recorded speech is "infant-directed", with intent, prosody, and/or emotional envelope directed towards infants (e.g., as in published literature disclosed below). Suggested and/or recorded speech is also infant directed and "active" with engagement of the intended reader in mind. In addition, content will meet age-appropriate norms for auditory content as in Table 1 (Below).

The audio output parameters for both English and foreign language pre-recorded age appropriate audio recordings are based upon the infant's age is disclosed Table 1, below:

TABLE 1

AGE BASED CHART FOR AUDIO CONTENT FOR AUDIO DEVICE

| Infant's Age | Audio Output Parameters 67, 75, for Audio Recordings 71 | |
| --- | --- | --- |
| 28-29 PMA start to 32 PMA | Total time per day: | 20 minutes |
| | Total time per week: | 3 to 4 times a week |
| | Appropriate content: | Simple songs with only 2 to 3 chords |
| | | Accapella - single voice |
| | | Sung at less than 60 bpm |
| | | Range of melody only 1 octave. |
| | | Stepwise melody, no intervals over a third. |
| | Volume: | Played at less than 55 dB on scale C |
| 32 PMA-36 PMA | Duration per audio emission: | 20 minutes |
| | Total time per day: | No more than 6 times per day (totaling 3 hours) |
| | Duration of silence: | at least 30 minutes |
| | Total time per week: | 5 days a week |
| | Appropriate content: | Simple songs with no more than 4 chords |
| | | Single voice and single instrumentation |
| | | Instrumentation played single notes not chords |
| | | Range of melody only 1 octaves. |
| | | Melody with no intervals over a 6th. |
| | Appropriate tempo: | Sung and played at less than 60 bpm. |
| | Volume: | Played at less than 55 dB on scale C |
| 36 PMA-40 PMA | Duration per audio emission: | 30 minutes |
| | Total time per day: | No more than 8 times per day (totaling 4 hours) |
| | Duration of silence: | Must have at least 30 minutes |
| | Total time per week: | 7 days a week |
| | Appropriate content: | Single voice and single instrumentation |
| | | Instrumentation must play single notes not chords |
| | | Range of melody only 1 octaves. |
| | | Melody with no intervals over a 6th. |
| | Appropriate tempo: | Sung and played at less than 60 bpm. |
| | Volume: | Played at less than 55 dB on scale C |
| 0 to 3 months | Duration per audio emission: | 30 minutes at a time |
| | Total time per day: | No more than 8 times per day (totaling 4 hours) |
| | Duration of silence: | Must have at least 30 minutes |
| | Total time per week: | 7 days a week |
| | Appropriate content: | Single voice and single instrumentation |
| | | Instrumentation can be multiple notes at once |
| | | No restrictions on melody range |

TABLE 1-continued

AGE BASED CHART FOR AUDIO
CONTENT FOR AUDIO DEVICE

| Infant's Age | Audio Output Parameters 67, 75, for Audio Recordings 71 | |
|---|---|---|
| | Appropriate tempo: | Sung and played at a more upbeat tempo between 60 to 120 bpm to promote playful mood |
| | Appropriate tempo: | Sung and played at less than 60 bpm to promote relaxation and sleep. |
| | Volume: | Played at less than 65 dB on scale C. |
| 3 to 6 months | Duration per audio emission: | 30 minutes at a time |
| | Total time per day: | No restrictions |
| | Duration of silence: | at least 30 minutes |
| | Total time per week: | Multiple voices and instrumentation (limit to 4) |
| | Appropriate content: | Recommend no sudden changes or sounds. No restrictions on melody range |
| | Appropriate tempo: | Sung and played at a more upbeat tempo between 60 to 120 bpm to promote playful mood |
| | Appropriate tempo: | Sung and played at less than 60 bpm to promote relaxation and sleep. |
| | Volume: | Played at less than 75 dB on scale C. |
| 6 to 12 months | Duration per audio emission: | 45 minutes at a time |
| | Total time per day: | No restrictions on how many times per day. |
| | Duration of silence: | Recommend at least 30 minutes |
| | Total time per week: | 7 days a week |
| | Appropriate content: | Multiple voices and instrumentation No restrictions on instrumentation or melody |
| | Appropriate tempo: | Sung and played at a more upbeat tempo between 60 to 120 bpm to promote playful mood |
| | Appropriate tempo: | Sung and played at less than 60 bpm to promote relaxation and sleep. |
| | Volume: | Played at less than 85 dB on scale C. |

The pressure threshold 69 parameters based upon the infant's age is disclosed Table 2, below:

TABLE 2

TABLE 2. PRESSURE THRESHOLD 69

| AGE | THRESHOLD PRESSURE mmHG | PAUSE TIME BEFORE STOP secs |
|---|---|---|
| 34-36 weeks | 5-15 | 10-15 |
| 36 weeks-3 months post term | 20-50 | 10 |
| 3-6 months | 50 | 5-10 |

Figure 6:
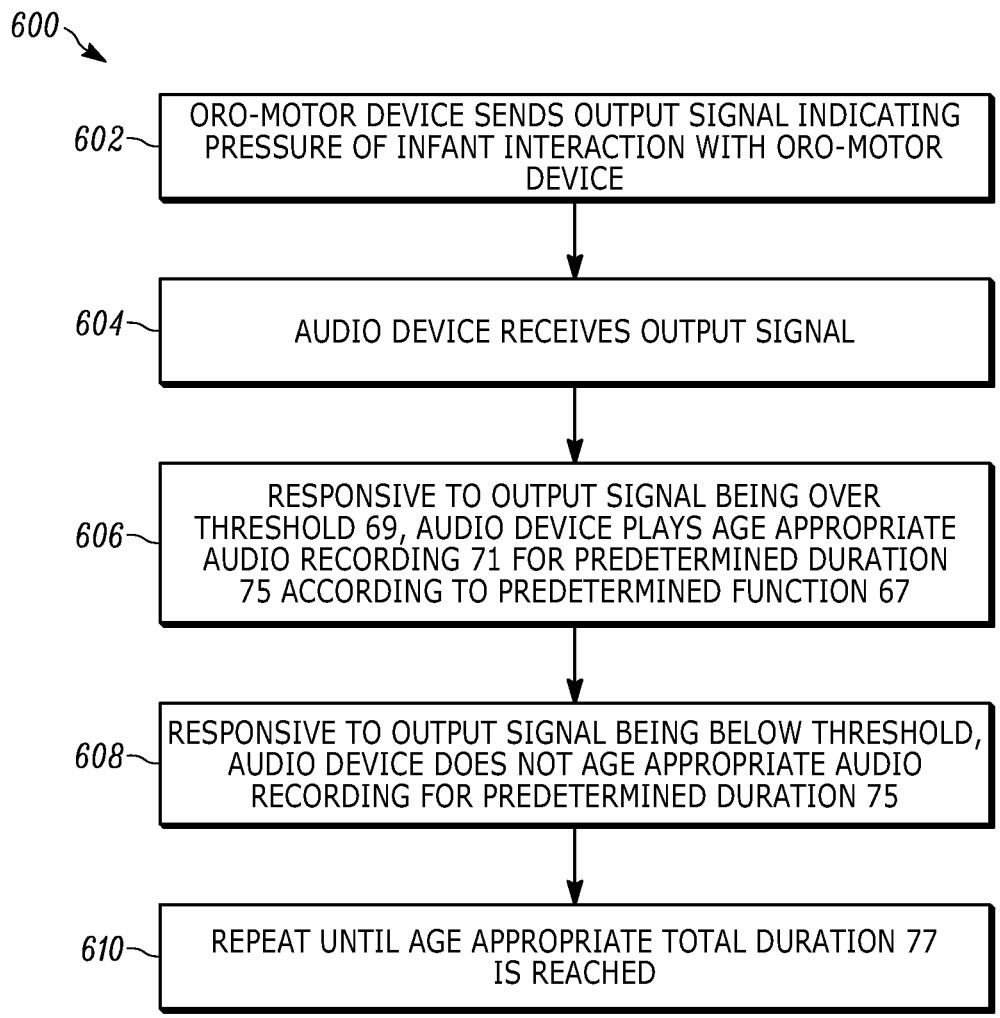
FIG. 6 illustrates a flow diagram for a method of utilizing an audio device in accordance with a first example embodiment of the present disclosure.

In FIG. 6, an example method 600 of oro-motor infant activated audio emission is illustrated. At 602, an oro-motor device 50, present in an awake infant's mouth, sends a signal indicating a pressure of an infant interaction with the nipple portion 52 of the oro-motor device. At 604, the audio device 10 receives the signal from the oro-motor device 50. At 606, responsive to the signal being over a threshold 69 (e.g., indicating the pressure applied by the infant is over the pressure threshold 69), the audio device 10 plays the age appropriate audio recording 71 for a predetermined duration 75. In one example embodiment, the predetermined duration 75 that is determined based upon the attention span of the preterm or premature infant (e.g., the predetermined duration 75 does not exceed the duration of the infant's attention span). At 608, responsive to the signal being below the threshold 69 (e.g., indicating the pressure applied by the infant is below the pressure threshold 69), the audio device 10 does not play the age appropriate audio recording 71 for a predetermined duration 75. At 610, steps 602-608 are repeated until the audio device 10 has played the age appropriate audio recording for an age appropriate total duration 77 (e.g., as determined based upon the infant's age and maturity and known attention spans of infants of that age and/or maturity).

Figure 7:
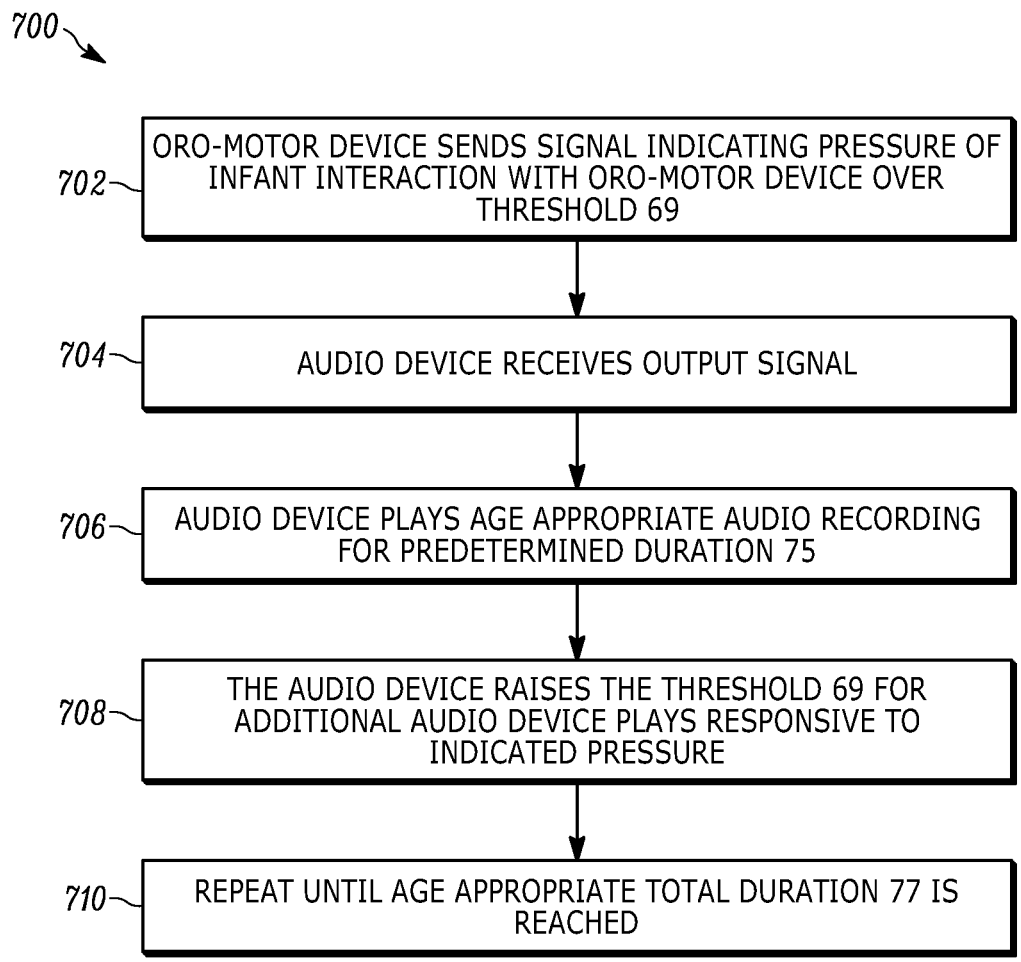
FIG. 7 illustrates a flow diagram for a method of utilizing an audio device in accordance with a second example embodiment of the present disclosure.

In FIG. 7, a second example method 700 of oro-motor infant activated audio emission is illustrated. At 702, the oro-motor device 50, present in an awake infant's mouth, sends a signal indicating a sensed pressure of an infant interaction with the nipple portion 52 is over the maturity and/or age appropriate predetermined threshold 69. At 704, the audio device 10 receives the signal from the oro-motor device 50. At 706, the audio device 10 plays the age appropriate audio recording for a predetermined duration 75. At 708, the audio device 10 raises the threshold 69 based upon the preterm/premature infant's previously measured pressure application to the nipple portion 52. For example, if the infant is sucking 5 mmHg above the threshold 69, then the threshold 69 will be raised to that pressure, or just below that pressure. In this example embodiment, one or more thresholds 69 are comprised in 5 mmHg increments. Thus, the oro-motor device 50 promotes better sucking behavior in the infant, and better captures the infant's attention, as the infant has to gradually increase their effort to receive caretaker's voice. At 710, steps 702-708 are repeated until the audio device 10 has played the age appropriate audio recording for an age appropriate total duration (e.g., as determined based upon the infant's age and maturity and known attention spans of infants of that age and/or maturity). In one example embodiment, the caretaker's voice is used to comfort or reassure an infant or child (such as when the infant or child is at daycare, in a hospital room, or otherwise separated from their caretaker) and/or help lull the infant or child to sleep. In another example embodiment, the caretaker's voice is used to help bring an infant or child out of anesthesia (e.g., without or without the oro-motor device 50). In yet another example embodiment, the caretaker's voice is used to educate an infant or child, by having the caretaker record audio comprising age appropriate information.

Figure 8:
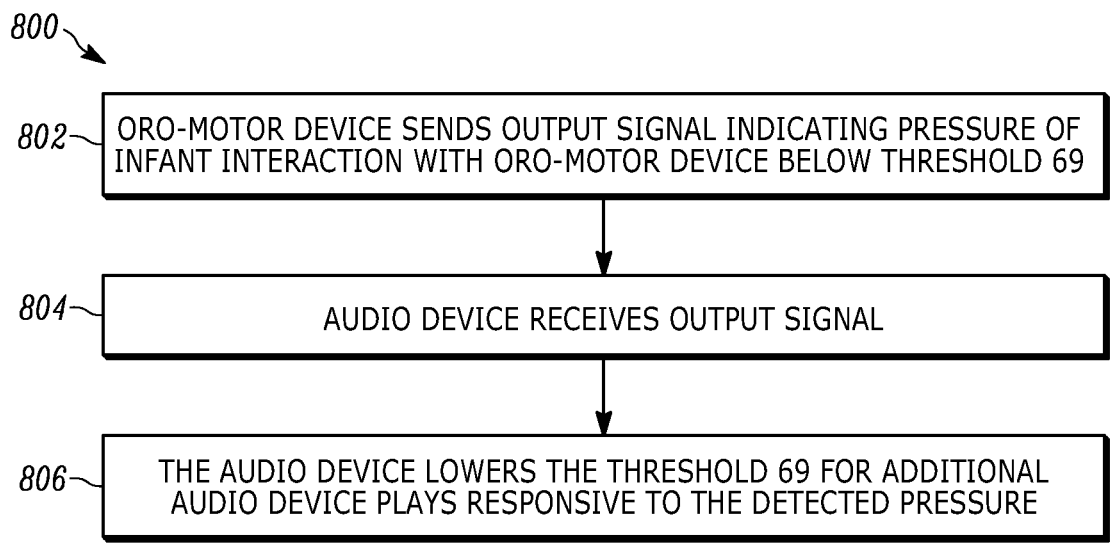
FIG. 8 illustrates a flow diagram for a method of utilizing an audio device in accordance with a third example embodiment of the present disclosure.

In FIG. 8, a third example method 800 of oro-motor infant activated audio emission is illustrated. At 802, the oro-motor device 50, present in an awake infant's mouth, sends a signal indicating a sensed pressure of an infant interaction with the nipple portion 52 is below the maturity and/or age appropriate predetermined threshold 69. At 604, the audio device 10 receives the signal 59 from the oro-motor device 50. At 706, the audio device 10 lowers the threshold 69 based upon the preterm/premature infant's previously measured pressure application to the nipple portion 52. For example, if the infant is sucking 5 mmHg below the threshold 69, then the threshold will be lowered to that pressure, or just below that pressure. By lowering the threshold 69 when needed, infants can be gradually taught to increase the pressure of their interactions with the nipple portion 52, to learn how to better suck on the nipple portion 52. Steps 706 is typically repeated until the audio device 10 has been signaled to play the age appropriate audio recording, based upon the infant's interaction with the nipple portion 52. Once the audio device 10 has been successfully signaled to place the age appropriate audio recording 71, the audio device will typically follow the method 700 steps 702-710. The methods 700 and 800, generate a feedback loop that will create customized infant protocols to teach the infants better sucking habits. The sucking habits of individual infants will be stored, and applied in subsequent sessions with the oro-motor device 50.

Figure 9:
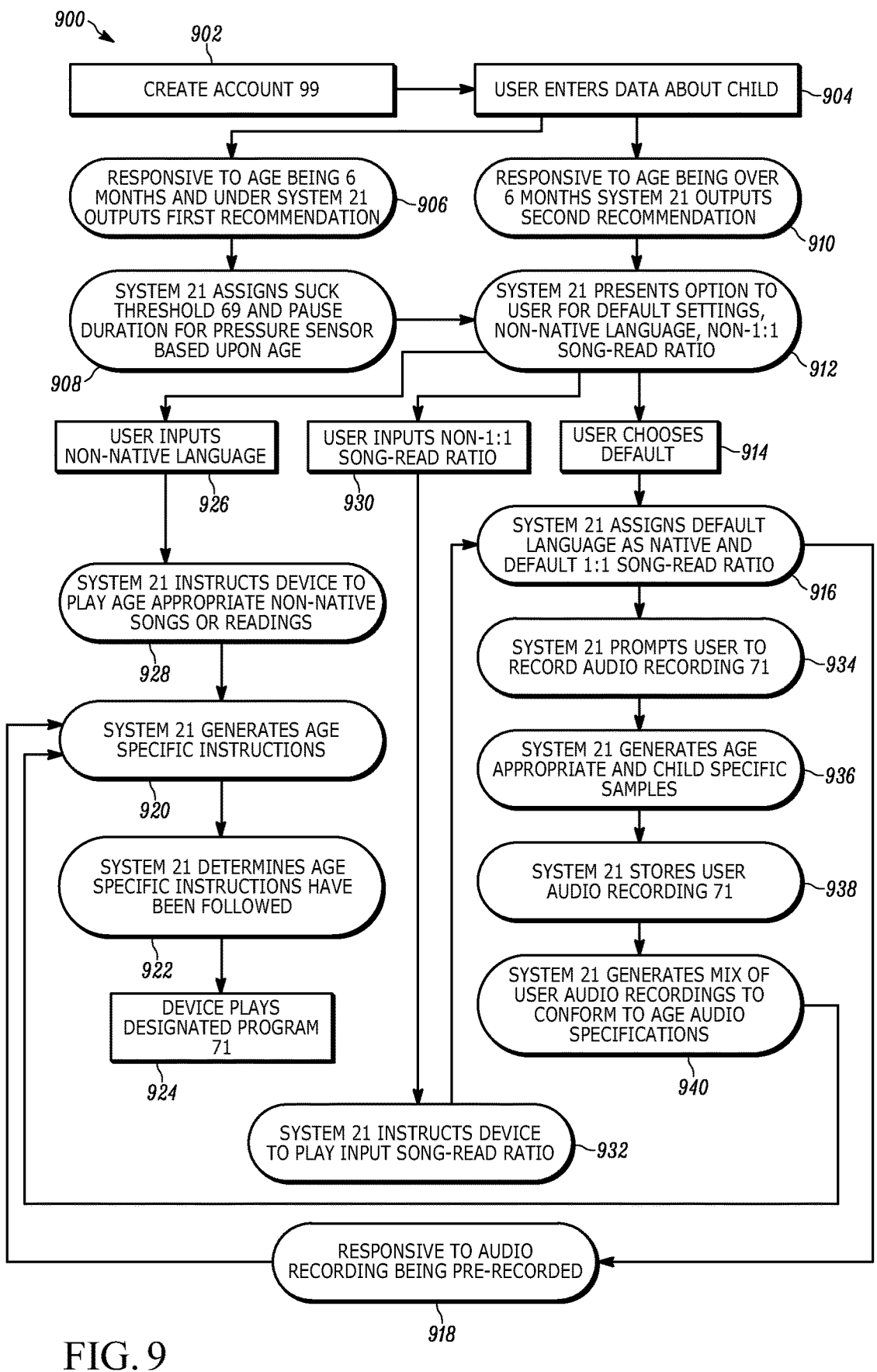
FIG. 9 illustrates a flow diagram for utilizing a system got use in an audio device in accordance with another example embodiment of the present disclosure.

In FIG. 9, an example system method 900 is illustrated. At 902, a user (e.g., a parent, a caretaker, etc.) creates an account 99 for a specific child. At 904 the user enters data about the specific child, including but not limited to, the child's name, age in months, a language preference, native language, and/or a song to reading ratio. At 906, responsive to the age of the specific child being 6 months and under, the language system 21 outputs a first recommendation. In this example embodiment, the first recommendation comprises using the oro-motor device 50 in conjunction with the audio device 10. At 908, the language system 21 assigns the suck threshold 69 and pause duration for the sensor 54 based upon the age of the specific child (see Table 2). At 912, the language system 21 instructs the interface 37 to present an option for the user to choose a default setting, a non-native language, and/or a non-1:1 song-read ratio. In some example embodiments, the user selects at least one of the default setting, the non-native language, and/or the non-1:1 song-read ratio when entering the data about the child at 904. At 914, the user chooses the default settings (e.g., native language and/or 1:1 song to read ratio). At 916, the language system 21 assigns the default language as the native language and the default ratio as 1:1. At 918, responsive to the user and/or others having pre-recorded audio recordings for the child, the language system 21, at 920, generates age specific instructions, and displays said instructions to the user via the interface 37 (e.g., placing the oro-motor 50 device in the child's mouth). At 922, responsive to the language system 21 determining age specific instructions have been followed, at 924, the audio device 10 plays a program 71 that correlates to the selections made by the user and the child's age (e.g., the default setting).

In some embodiments, new users, users who want to alter their age-appropriate audio recordings 71, and/or users whose children have aged into new parameters record new audio recordings. At 934, the language system 21 prompts the user to record an audio recording. In one example embodiment, the user is familiar with how to record the audio recording 71, and what is appropriate subject matter (see, Table 1). At 936, responsive to the user selecting a provide examples option, the language system 21 generates age appropriate and child specific examples of infant directed speech (e.g., including the child's name). In this example embodiment, the user follows the instructions, including instructions to engage in active reading. In one example embodiment, the instructions comprise between 1-20 instructions for recordable subject matter. At 938, the user recites the examples and the language system 21 stores the user's audio recordings (e.g., in a memory component of the microcomputer 32, in a remote location that is accessible to the microcomputer 32, etc.). At 940, the language system 21 generates a mix of user audio recordings to generate an age appropriate audio recording conforming to Table 1. At 920, the language system 21 generates age specific instructions, and displays said instructions to the user via the interface 37 (e.g., placing the oro-motor 50 device in the child's mouth). At 922, responsive to the language system 21 determining age specific instructions have been followed, at 924, the audio device 10 plays a program comprising the user's audio recording and/or the mixed user's audio recording, that correlates to the selections made by the user and the child's age (e.g., duration of play, song to reading ratio, etc.).

At 910, responsive to the child's age being over 6 months, the language system 21 outputs a second recommendation. In one example embodiment, the second recommendation comprises utilizing a hand held sensor rather than the oro-motor device 50. One suitable example of the hand-held-sensor is a scaled up oro-motor device 50 in which the nipple 52 is large enough to be squeezed by the infant to provide varying output signals 59. In one example embodiment, the hand-held-sensor comprises a ball or toy having an interactive sensor. The interactive sensor comprising at least one of a pressure sensor, a tilt sensor, or accelerometer. In another example embodiment, the hand-held-sensor comprises a mat or other device that comprises the interactive sensor. In an example embodiment, the hand-held-sensor is a variation that is used by older children and/or adults. In another example embodiment, the hand-held-sensor and the oro-motor device 50 are referred to collectively as sensing device. At 930, the user selects the non-1:1 song-read ratio.

At 926, the user inputs the non-native language option. At 928, responsive to the user inputting the non-native language option, the language system 21 instructs the audio device 10 (e.g., via the microcomputer) to play an age appropriate non-native song and/or reading as determined by Table 1. In one example embodiment, the language system 21 provides the user with the age appropriate non-native song and/or reading comprising infant directed speech, active reading, and/or singing from a native non-native language speaker. At 920, the language system 21 generates age specific instructions, and displays the instructions to the user via the interface 37 (e.g., placing the oro-motor 50 device in the child's mouth, placing the hand-held-sensor into a child's or adult's hand or within their reach). At 922, responsive to the language system 21 determining age specific instructions have been followed, at 924, the audio device 10 plays a program of infant directed speech that correlates to the selections made by the user and the child's age (e.g., duration of play, song to reading ratio, language, etc.).

At 932, responsive to the user selecting the non-1:1 song-read ratio and the user also selecting the non-native language, the language system 21 instructs the audio device 10 via the microcontroller 32 to play sounds based upon the user's input song-read ratio and language selection. Responsive to the user also selecting the non-native language, the language system 21 will proceed to method step 920. Responsive to the user selecting solely the non-1:1 song-read ratio, the language system 21 proceeds to the method step 934 and proceeds as described above with regards to methods steps 934-940, 920-924.

The audio device 10 allows for a voice recognition by presenting parent's voices to infants when parents cannot be with the infant while simultaneously promoting active learning in the infant, by presenting the parent's voice in response to successful sucking. Infant-directed speech sounds are known to improve language development of the infants, and active learning using the combination of suck activated directed speech and parental speech recognition promotes better verbal outcomes of preterm and/or premature infants at two years of age. At many hospitals parental visitation happens infrequently and for small time periods. The audio device 10 allows infants to receive their parents' speech, in a safe and developmentally appropriate manner while teaching aid infants how to suck and focus on the speech. Further, because the audio device 10 may be programmed to emit audio at the preset decibel level, for the preset duration, and at the preset intervals, inappropriate (e.g., too loud, too long, too frequent) sound exposure can be avoided. Inappropriate sound exposure can damage brain development of infants. Additionally, where a caretaker or parent chooses pre-recorded age appropriate audio recordings in a specific foreign language, the infant or child showed marked sound differentiation ability to differentiate that specific language after twenty (20) sessions, and will be primed to acquire language skills both speaking and understanding in that specific language as they age and develop language skills.

The bilingual brain benefit is developed during infancy, when the brain plasticity for language is highest. Infants, from even before birth, specialize their brain's ability to differentiate phonemes (speech sounds) of different languages. However as infants age, their brains specialize to the native language(s) that they are exposed to during infancy. Typically, there are 800 different speech sound that are drawn upon across multiple languages, with an average language utilizing between about 40-70 different speech sounds. In the case of English, approximately 44 speech sounds are utilized. Typically, an infant raised in a monolingual household will lose the ability to differentiate the speech sounds not used in their native language, and therefore lose the ability to create those same speech sounds when they do begin speaking. When a child is exposed to multiple languages during infancy, for example by the audio device 10, the brain develops an ability to recruit other parts of the brain to process language, and suppress one set of speech sounds in favor of another set depending on which language (s) the infant is exposed to (e.g., utilizing executive function, which is associated with decision making, attention span, and/or delaying the onset of dementia and Alzheimer's in late life). An infant exposed to multiple languages will have a brain that more easily learns the specific non-native language that the infant was exposed to, as well as have an overall advantage for learning non-native languages (e.g., non-native languages the infant was not exposed to). This is discussed further in Kovacs, A. M., and J. Mehler. "*Cognitive Gains in 7-Month-Old Bilingual Infants.*" Proceedings of the National Academy of Sciences, vol. 106, no. 16, 2009, pp. 6556-6560., doi:10.1073/pnas.0811323106; Kovacs, A. M., and J. Mehler, "*Cognitive Gains in 7-Month-Old Bilingual Infants.*" Proceedings of the National Academy of Sciences, vol. 106, no. 16, 2009, pp. 6556-6560., doi: 10.1073/pnas.0811323106; Kalashnikova, Marina, et al. "*Infant-Directed Speech Facilitates Seven-Month-Old Infants' Cortical Tracking of Speech.*" Scientific Reports, vol. 8, no. 1, 2018, doi:10.1038/s41598-018-32150-6, and Kalashnikova, Marina, et al. "*Infant-Directed Speech Facilitates Seven-Month-Old Infants' Cortical Tracking of Speech.*" Scientific Reports, vol. 8, no. 1, 2018, doi:10.1038/s41598-018-32150-6.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 10%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method of utilizing an oro-motor device to activate an audio device, the method comprising the steps of:

providing an oro-motor device comprising a sensor and a depressible portion producing an output signal when said depressible portion is compressed yielding a first measured pressure over an age appropriate predetermined threshold applied to the depressible portion;

responsive to said output signal, playing an age appropriate audio recording for a predetermined duration on an audio device; and increasing the age appropriate predetermined threshold to a raised threshold proportionally to a difference between the first measured pressure to the depressible portion and the age appropriate predetermined threshold.

2. The method of claim 1, further comprising the step of signaling that the oro-motor device has had a second measured pressure below the age appropriate predetermined threshold applied to the depressible portion.

3. The method of claim 2, responsive to said signaling, lowering the age appropriate predetermined threshold to a lowered threshold proportionally to a difference between the first measured pressure application to the depressible portion and the age appropriate predetermined threshold.

4. The method of claim 1, further comprising the step of playing the age appropriate audio recording for the predetermined duration, wherein the predetermined duration is between 5 seconds to 25 seconds.

5. The method of claim 1, further comprising the step of limiting daily playing of the age appropriate audio recording to an age appropriate total duration, wherein the age appropriate total duration is between one half hour to about 1 hour.

6. The method of claim 1, wherein the playing an age appropriate audio recording comprises at least one of:
   playing a recording of a voice of a caretaker; and
   providing and playing an age appropriate audio recording in a foreign language.

7. The method of claim 1, wherein the providing the depressible portion comprises providing at least one of a nipple, a ball, and a mat.

8. A non-transitory computer readable medium storing machine executable instructions for utilizing an oro-motor device to activate an audio device comprising:
   a language system in electronic communication with the audio device, a sensing device comprising a sensor, and an interface, the interface configured to receive user data and the sensing device configured to send signals to the language system, the language system providing at least one of:
      a first recommendation or a second recommendation for sensing device sensor usage;
      a sensor threshold and sensor readings of the sensing device;
      a duration of audio output; and
      specific parameters for audio output; and
   the language system based upon the signal from the sensing device, indicating the sensor threshold has been exceeded, sends instructions to the audio device to emit an appropriate audio recording that conforms to the specific parameters for audio output for the assigned duration of audio output.

9. The non-transitory computer readable medium of claim 8 wherein the language system instructs the interface to offer at least one of a default option, a non-native language option, and a non 1:1 read-song ratio to a user.

10. The non-transitory computer readable medium of claim 9 wherein responsive to the language system receiving instructions to provide the non-native language option, the language system provides non-native language songs and readings that conform to the identified specific parameters, and instructs the audio device to emit audio comprising the non-native language songs and readings for the assigned duration.

11. The non-transitory computer readable medium of claim 9 wherein responsive to the language system receiving instructions to provide the non 1:1 read-song ratio option, the language system generates a read-song mix that corresponds to a selected song to reading ratio, and instructs the audio device to emit audio comprising the read-song mix for the assigned duration.

12. The non-transitory computer readable medium of claim 9 wherein responsive to the language system receiving instructions to provide the default option, the language system generates a pre-recorded audio recording that corresponds to the default song to reading ratio and the default language, and instructs the audio device to emit audio comprising the default song to reading ratio and the default language for the assigned duration.

13. The non-transitory computer readable medium of claim 9 wherein responsive to the language system receiving instructions to provide the default option, the language system generates samples of appropriate subject matter to be recorded by a user, and sends instructions to the audio device to record the user reciting the samples to generate user recordings.

14. The non-transitory computer readable medium of claim 13, wherein the samples comprise user input data comprising at least one of a child's name, songs selected based upon a child's age, and readings selected based upon a child's age.

15. The non-transitory computer readable medium of claim 13, wherein the language system at least one of alters and combines the user recordings to conform to the specific parameters for audio output to comprise altered or combined user recordings, the altered or combined user recordings comprises the appropriate audio recording.

16. A language system comprising an audio device coupled an oro-motor device, the system comprising:
   the oro-motor device comprising a nipple housing a sensor, wherein the sensor produces an output signal when said nipple portion compressed to a pressure over a first measured pressure over an age appropriate predetermined threshold;
   the audio device comprising a microcomputer in electrical communication with the oro-motor device, a microphone, a speaker, and an interface, the microcomputer comprising a language system, the language system responsive to a user input received via the interface, assigns a sensor threshold and sensor readings of the oro-motor device, assigns a duration of audio output, and identifies specific parameters for audio output, the language system based upon the output signal from the oro-motor device indicating the age appropriate predetermined threshold has been exceeded, sends instructions to the audio device to emit an appropriate audio recording that conforms to the specific parameters for audio output for the assigned duration of audio output.

17. The language system of claim 16, wherein the specific parameters for audio output comprise at least one of an age dependent volume, an age dependent number of intervals per day and per week, and age appropriate content.

18. The language system of claim 16, wherein the language system raises the age appropriate predetermined threshold to a raised threshold proportionally to a difference between a first measured pressure application to the nipple portion and the age appropriate predetermined threshold.

19. The language system of claim 16, wherein the interface displays an option to emit audio comprising at least one of a default recording, a non-native language recording, and a non-default read-song ratio recording to the user.

20. The language system of claim 16, wherein responsive to the user selecting the non-native language recording, the language system identifies non-native language songs and readings that conform to the identified specific parameters, and instructs the audio device to emit audio comprising the non-native language songs and readings for the assigned duration.

* * * * *